United States Patent [19]

Kawaguchi

[11] Patent Number: 4,621,029
[45] Date of Patent: Nov. 4, 1986

[54] MEDICAL SEALANT FOR SKIN

[75] Inventor: Nobuhisa Kawaguchi, Kamakura, Japan

[73] Assignee: Fuji Systems Corporation, Tokyo, Japan

[21] Appl. No.: 690,583

[22] Filed: Jan. 11, 1985

[30] Foreign Application Priority Data

Jan. 17, 1984 [JP] Japan .................................. 59-4789

[51] Int. Cl.$^4$ .............................................. B32B 9/04
[52] U.S. Cl. ...................................... 428/447; 428/40;
428/60; 524/432; 524/588; 524/783; 524/858;
524/859; 524/860; 524/862; 528/15; 528/18;
528/24; 528/31; 528/32; 528/33; 528/34;
528/901
[58] Field of Search ................... 528/24, 18, 34, 901,
528/15, 31, 32, 33; 524/432, 588, 783, 858, 859,
860, 862; 428/447, 40, 60

[56] References Cited

U.S. PATENT DOCUMENTS

| | | | |
|---|---|---|---|
| 4,316,941 | 2/1982 | Eguchi et al. | 428/392 |
| 4,322,320 | 3/1982 | Caprino | 524/432 |
| 4,460,371 | 7/1984 | Abber | 428/355 |
| 4,526,922 | 7/1985 | Pickwell et al. | 528/24 |

Primary Examiner—Melvyn I. Marquis
Attorney, Agent, or Firm—Murray and Whisenhunt

[57] ABSTRACT

This invention relates to a medical sealant comprising polyorganosiloxane gel for sealing a junction part between living skin and a medical instrument penetrating through the skin, said polyorganosiloxane gel having a partially cross-linked three dimentional structure expressed by the basis general formula of $$R_n SiO_{(4-n)/2}$$

(wherein R represents hydrogen or monovalent hydrocarbonyl group and n represents an integer of 1 to 3), characterized in that said gel self-supports its figure at room temperature and has a hardness expressed by a loading weight of 1 g to 250 g by which a disc of a diameter of 10 mm sinks to 1.0 mm on the gel.

11 Claims, 4 Drawing Figures

MEDICAL SEALANT FOR SKIN

BACKGROUND OF THE INVENTION

This invention relates to a medical sealant for skin.

Techniques for penetrating medical instruments, for example, solid supporters, lead wires, tubings such as catheters and the like through living bodies have been widely used lately in proportion to the development of internal organs. However, the part of a living body through which a medical instrument such as a catheter is introduced from the outside of the body into the inside is liable to be contaminated. Particularly, when the medical instrument is inserted into the living body for a long time, the inserted part of the living body is easily infected with bacteria during extension movement, bathing and the like. Thus, many patients and doctors are worried about this type of infection with bacteria.

This problem is severe particularly when a medical instrument such as a catheter, lead wire and the like is penetrated through the skin other than opening parts of a human body such as a urethra, anus, nostril and the like.

SUMMARY OF THE INVENTION

An object of the present invention is to dissolve the above mentioned problem by providing a medical sealant for sealing a junction part between living skin and a medical instrument penetrating through the skin without being detrimental to living body. Thus, the object of the present invention is to provide a medical sealant comprising polyorganosiloxane gel for sealing a junction part between living skin and a medical instrument penetrating through the skin, said polyorganosiloxane gel having a partially cross-linked three dimentional structure expressed by the basis general formula of $$R_nSiO_{(4-n)/2}$$

(wherein R represents hydrogen or monovalent hydrocarbonyl group and n represents an integer of 1 to 3), characterized in that said gel self-supports its figure at room temperature and has a hardness expressed by a loading weight of 1 g to 250 g by which a disc of a diameter of 10 mm sinks to 1.0 mm on the gel.

It is essential for the polyorganosiloxane gel of the present invention to have almost the same hardness as that of human skin.

DETAILED DESCRIPTION OF THE INVENTION

Figure 1:
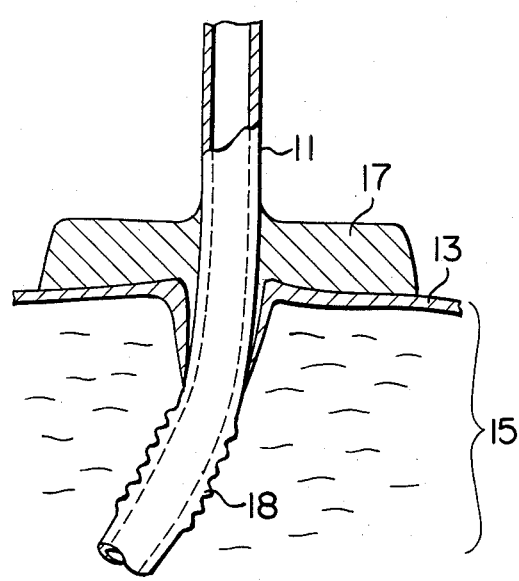
FIGS. 1, 3 and 4 are sectional views illustrating the preferred embodiments of the present invention.

Polyorganosiloxane is substantially non-reactive to living body and accordingly very safe in the use of being made contact with human skin. Its oily product is widely used for a protective skin cream and other cosmetics. Since polyorganosiloxance has not only safety but also other useful properties such as water-resistance, weather-resistance, heat-resistance and the like, its rubber-like product is widely used for medical instruments, packing, electric wire and the like.

The medical sealant of the present invention comprises a polyorganosiloxane gel having a partially cross-linked three dimentional structure expressed by the basic general formula of $$R_nSiO_{(4-n)/2}$$

(wherein R represents hydrogen or monovalent hydrocarbonyl group and n represents an integer of 1 to 3), characterized in that said gel self-supports its figure at room temperature and has a hardness similar to that of human skin, that is, a hardness expressed by a loading weight of 1 g to 250 g by which a disc of a diameter of 10 mm sinks to 1.0 mm on the gel.

Examples of the monovalent hydrocarbonyl group include methyl, vinyl, phenyl and the like. Preferably, the major part of the hydrocarbonyl group is methyl and a very minor part of the hydrocarbonyl group is vinyl, phenyl and the like.

Any conventional polyorganosiloxane can be used for preparing the medical sealant of the present invention, but it is absolutely essential that the organopolysiloxane gel used in the present invention should self-support its own figure and have a hardness expressed by a loading weight of 1 g to 250 g by which a disc of a diameter of 10 mm sinks to 1.0 mm on the gel.

A preferable polyorganosiloxane gel can be prepared by partially cross-linking linear polyorganosiloxane having the general formula,

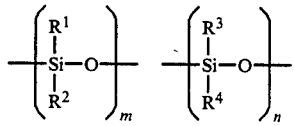

wherein $R^1$, $R^2$, $R^3$ and $R^4$ may be the same or different, and represent hydrogen, monovalent hydrocarbonyl group, alkoxy, acyl, hydroxyl and the like.

Example of the hydrocarbonyl group include alkyl such as methyl, vinyl, phenyl and the like, and the carbon number of the hydrocarbonyl group is preferably not more than 6. The number of m and n may be appropriately selected. The major part of $R^1$, $R^2$, $R^3$ and $R^4$ bonded with the silicon atoms of the polyorganosiloxane should preferably be methyl.

The linear polyorganosiloxane should have a viscosity of 1,000 cs to 1,000,000 cs at 25° C. If the viscosity is less than 1,000 cs, the cross-linked polyorganosiloxane obtained therefrom is weak, fragile and liable to crack. On the other hand, if the viscosity is higher than 1,000,000 cs, it is too hard and is almost impossible to cast.

Any conventional cross-linking agent can be used for cross-linking the linear polyorganosiloxane, but examples of a preferable cross-linking agent include ethylorthosilicate, propylorthosilicate and the like.

Examples of cross-linking reaction of polyorganosiloxane are illustrated below. Any reaction of the following examples can be used.

(1) Dealcohol reaction with hydroxyl group:

-continued organic tin compound wherein $R^5$ represent an alkyl group.

(2) Cross-linking reaction on the basis of vinyl group:

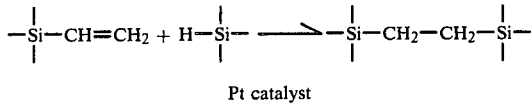

Pt catalyst (3) Dehydration reaction between hydroxyl groups:

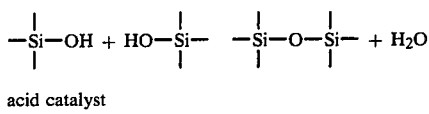

acid catalyst (4) Radical reaction by organic peroxide:

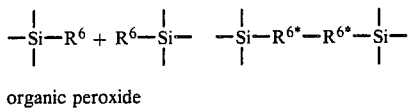

organic peroxide wherein $R^6$ represents an alkyl group and $R^{6*}$ represents an alkylene group on the basis of $R^6$ after radical reaction.

This reaction may be carried out by the action of radiation.

The cross-linking reactions of the above types (1) and (2) can be effected at a temperature from room temperature to about 100° C. The cross-linking reactions of the above types (3) and (4) are usually effected by heating at 100° C. to 200° C., except for the reaction by the action of radiation. Any type of the above reactions can be used for the purpose of the present invention.

These reactions are more fully disclosed in "Plastic Techniques Complete Book: Silicone Resin" published on July 10, 1971 by Kabushiki Kaisha Kogyo Chosa-kai Shuppan.

Polyorganosiloxane used in the present invention is modified in such a manner as to provide a loose three dimentional structure by controlling contents of vinyl, hydroxyl and other groups, changing cross-linking conditions and/or adding a silicone oil such as polydimethylsiloxane.

The polyorganosiloxane gel thus modified is sticky and has a hardness expressed by a loading weight of 1 g to 250 g by which a thin metallic disc of a diameter of 10 mm sinks to 1.0 mm on the gel.

The hardness of the polyorganosiloxane gel thus obtained should preferably be almost the same as that of a living body or a little softer. If the hardness as defined above is less than 1 g load, the gel is too soft and does not self-support its figure, thus being unsuitable as a sealant. On the other hand, if the hardness is more than 250 g load, the gel is too hard and causes insufficient adhesion to human skin.

The polyorganosiloxane sealant composition used in the present invention generally comprises 100 parts by weight of reactive polyorganosiloxane and an effective amount of not exceeding 500 parts by weight, preferably 100 to 300 parts by weight of polydimethylsiloxane (silicone oil) as the main components. The composition may further contain an effective amount of not exceeding 5% by weight of a cross-linking agent and an effective minor amount of catalyst.

The composition optionally contains zinc oxide, medicines for external application, sterilizers, and the like.

If polydimethylsiloxane (silicone oil) is not added, the sealant often becomes too hard. On the other hand, if the amount of silicone oil exceeds 500 parts by weight, the sealant becomes too soft and not self-supportable.

Polydimethylsiloxane (silicone oil) used to modify polyorganosiloxane should have a viscosity of 20 to 50,000 cs, preferably 20 to 1,000 cs. If the viscosity of the silicone oil is less than 20 cs, the silicone becomes too volatile for a practical use. On the other hand, if the viscosity of the silicone oil is more than 50,000 cs, the silicone becomes too viscous for handling.

It is essential for the present invention that the polyorganosiloxane should be self-supportable at a temperature of from room temperature to about 45° C. so that one can freely conduct daily life, for example, taking a bath, without suffering from any trouble.

Thus, the polyorganosiloxane used in the present invention should have an appropriate stickiness for satisfactory sealing and an appropriate hardness for easy handling. Also, this must be durable for sealing for a long time.

The polyorganosiloxane sealant is used in a relatively small size, and a typical example is a cylinder shape having a diameter of 10 mm and a thickness of 10 mm.

The sealant of the present invention is prepared by casting polyorganosiloxane together with a cross-linking agent in a mold, for example box-like mold, and causing a cross-linking reaction to gel at room temperature or in the presence of heat. The shape of gel is optionally selected depending on use, and a popular shape is sheet-like. The gel may be reinforced with an appropriate backing sheet, for example, plastic film such as polyester, woven or non-woven sheet made of natural or synthetic fibers. The gel reinforced with a backing sheet has such advantages as that it becomes not only strong but also convenient in handling regardless of being sticky. The gel reinforced with a backing sheet is prepared by placing a backing sheet in a mold and casting polyorganosiloxane reactants thereon to gel. Since gel of the present invention is highly sticky, it is sometimes hard to remove the product from a mold. Polyorganosiloxane composition may be gelled on water at room temperature since the specific gravity of the composition is less than that of water. For example, a polyorganosiloxane gel sheet can be obtained by floating a frame of polystyrene on water, casting therein polyorganosiloxane composition cross-linkable at room temperature and taking out the product from the frame. A backing sheet may further be placed thereon after gelling.

As a sealant of the present invention is highly adhesive, it is convenient to wrap the sealant with an appropriate wrapping paper for use as a final product. The wrapping paper used should not be adhesive to the gel. Examples of the wrapping paper practically usable include synthetic resin foam sheet such as urethane foam, polyethylene film and fluorocarbon resin sheet such as polytetrafluoroethylene (Teflon) resin film. These films may be coated with a soap as a releasing agent.

The sealant gel may contain zinc oxide (zinc flowers), medicines for external application, sterilizers and the like depending on use. Zinc oxide has a weak astringent property to a human skin, thereby preventing rash. This is used in an amount of 0 to 30% by weight in the sealant gel.

FIG. 1 is a sectional view illustrating the state of the junction part between skin and a conduit sealed with the sealant of the present invention.

Figure 2:
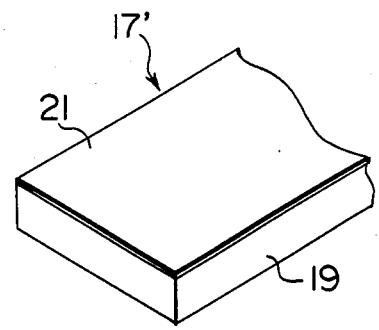
FIG. 2 illustrates a sample of the sealant of the present invention, which is reinforced with a backing sheet.

As seen from FIG. 1, catheter 11 having flexible part 18 is penetrated through skin layer 15 into living body. Sealant 17 is previously perforated in such a manner so to fit the size of catheter 11, and is then adhered to skin 13 to seal the junction part between catheter 11 and skin layer 15. Since sealant 17 is highly sticky, it is convenient in handling if sealant gel 19 is reinforced with backing sheet 21 to prepare the backed sealant 17' as shown in FIG. 2.

Figure 3:
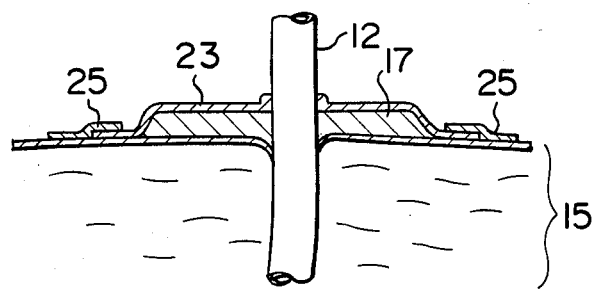

FIG. 3 is a cross sectional view showing another embodiment wherein sealant 17 sealing the junction part between wire 12 and skin layer 15 is covered with cover 23 to prevent sealant 17 from adhering to clothes. Cover 23 may further be fixed by any conventional adhesive tape 25 to prevent sealant 17 from releasing when stress is applied to an inserted medical instrument such as catheter, wire 12 and the like. Examples of cover 23 and 23' include plastic, rubber cover and the like.

Figure 4:
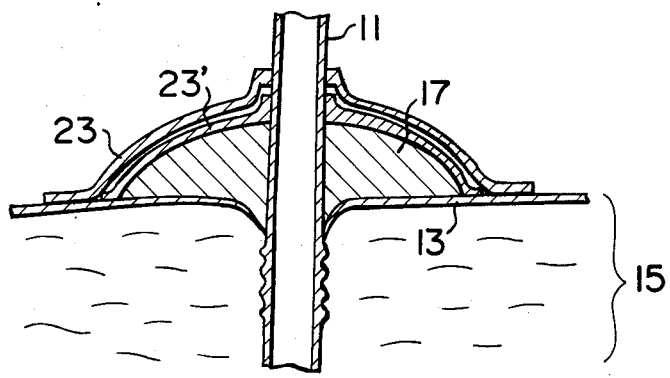

FIG. 4 is also a cross sectional view showing still another embodiment wherein sealant 17 sealing the junction part between skin layer 15 and catheter 11 penetrating through the skin layer is doubly covered with rubber cover 23' and plastic cover 23.

As mentioned above, the sealant of the present invention completely seals the junction part between human skin and a medical instrument inserted therethrough without being detrimental to living body, thus preventing infection with bacteria. The sealing effect in accordance with the present invention can be maintained for a long time. As silicone has excellent water-repellent and water-resistant properties, a patent with a medical instrument attached can freely take a bath.

The sealant of the present invention is furthermore widely used for sealing wire, catheter, and other medical instruments used in connection with the junction of artery and vein in artificial dialysis, artificial lung, peritoneum dialysis, artificial heart and other orthopedic treatment.

The present invention is further illustrated by the following Examples, but should not be limited thereto.

EXAMPLE 1

100 parts by weight of polydimethylsiloxane of a viscosity of 15,000 cs at 25° C. having a terminal hydroxyl group, 2 parts by weight of normal propyl orthosilicate, 0.5 part by weight of stannous octoate (tin content 28%) and 200 parts by weight of polydimethylsiloxane of a viscosity of 1,000 cs at 25° C. were fully mixed. The resultant mixture was cast in the center of a wooden frame of an inside size of 10 cm × 10 cm floated on water, and the cast mixture was allowed to stand for 30 minutes at normal temperature to gel, thus obtaining a sheet-like sealant having a thickness of about 5 mm. The hardness of the sealant thus obtained was about 15.5 g load. The sealant was then held between urethane foam sheets, and a disk of a diameter of 30 mm was cut out by a scissors making a hole in the center. Peeling off the urethane foam sheet, the sealant was applied to a silicone catheter inserted through the belly median line of a patient of peritoneum dialysis by passing the catheter through the hole of the sealant. The sealant thus applied on the junction part between the catheter and human skin was then covered with gauze and was fixed with an adhesive tape.

After 60 days from the treatment, there was no detrimental influence on the skin. The sealant was kept clean by exchanging gauze, and the softness of the sealant was not changed. It was possible to take a bath for four times, thus the sealing effect being complete.

EXAMPLE 2

100 parts by weight of polydimethylsiloxane of a viscosity of 18,000 cs having vinyl groups on both terminal ends, 8 parts by weight of polysiloxane (methyl hydrogen polysiloxane comprising 10 mol % of trimethyl siloxane, 40 mol % of dimethyl siloxane and 50 mol % of methyl hydrogen siloxane), 0.3 part by weight of an isopropyl alcohol solution of chloroplatinic acid (platinum content 1%) and 270 parts by weight of polydimethylsiloxane having a molecular weight of about 50,000 were fully mixed to prepare an addition reaction type silicone gel. The resultant mixture was cast on a 100 mesh polyester backing sheet placed in a mold to prepare a sealant sheet having a thickness of 2 mm. The hardness of the gel thus obtained was about 50 g load. The gel sheet was then perforated to make a hole of a diameter of 4.9 mm in the center, and was placed on a silicone rubber disk sheet having a diameter of 50 mm and a thickness of 1.5 mm. The sealant covered with the silicone rubber was then used to seal the junction part between a human skin and a urethral catheter inserted in the body by making the gel surface come into contact with the skin. Thereafter, 6 sheets of gauze were placed on the back of the silicone rubber disk and the sealant system was fixed onto the skin by an adhesive tape. After 4 weeks from the treatment, any rash by the leakage of urine was not caused, and no infection with bacteria was caused even after taking a bath twice.

EXAMPLE 3

The procedure of Example 2 was repeated, except that 5% by weight of zinc flower was mixed with the addition reaction type silicone gel of Example 2 to prepare a sealant sheet having a thickness of 5 mm.

The sealant sheet thus obtained was attached to the inside of the upper arm of a boy of adult. Even after 6 days from the application, there was no adverse effect on the skin and the stickiness of the sealant to the skin did not change at all.

What we claim is: 1.

1. A medical sealant having a thickness of at least 2 mm comprising polyorganosiloxane gel for sealing a junction part between living skin and a medical instrument penetrating through the skin, said polyorganosiloxane having a three dimensional structure expressed by the general formula

$$R_nSiO_{(4-n/2)}$$

wherein R represents hydrogen or monovalent hydrocarbon group having not more than 6 carbon atoms and n represents an integer of 1 to 3, characterized in that said gel contains an effective amount of a silicone oil, not exceeding 500 parts by weight of silicone oil per 100 parts by weight of said polyorganosiloxane gel so that the sealant has a hardness expressed by a loading weight of 1 g to 250 g by which a disc of a diameter of 10 mm sinks to 1.0 on the gel.

2. The sealant according to claim 1 further comprising a backing sheet supporting said polyorganosiloxane gel.

3. The sealant according to claim 1 further comprising a medicine for external application.

4. The sealant according to claim 1 further comprising a sterilant.

5. The sealant according to claim 1 further comprising zinc oxide.

6. The medical sealant according to claim 1, wherein an amount of said silicone oil added is 100 to 300 parts by weight per 100 parts by weight of said polyorganosiloxane gel.

7. The medical sealant according to claim 1, wherein said silicone oil is polydimethylsiloxane having a viscosity of 20 to 50,000 cs.

8. The medical sealant according to claim 7, where said polydimethylsiloxane has a viscosity of 20 to 1,000 cs.

9. A self-supporting, human skin adherable, medical sealant member having a thickness of at least 2 mm for interposition between living skin and a medical instrument penetrating through said skin to seal a juncture between said skin and said medical instrument penetrating through said skin, said medical sealant member comprising a polyorganosiloxane gel having a three dimensional structure expressed by the formula

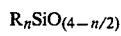

wherein R represents hydrogen or monovalent hydrocarbon group and n represents an integer of 1 to 3 consisting essentially of a linear polyorganosiloxane having the formula

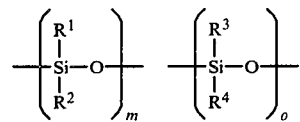

wherein $R^1$, $R^2$, $R^3$ and $R^4$, which may be the same or different, represent hydrogen, monovalent hydrocarbon, alkoxy, acyl or hydroxyl, and m and o are numbers chosen so that the viscosity of the linear polyorganosiloxane is in the range of from 1,000 cs to 1,000,000 cs at 25° C., cross-linked in the presence of a polydimethylsiloxane having a viscosity in the range of 20 cs to 50,000 cs, said polydimethylsiloxane being present in an amount, not exceeding 500 parts by weight per 100 parts by weight of linear polyorganosiloxane, effective to produce a gel having a hardness such that the weight necessary to sink a disc of 10 mm diameter 1 mm into the gel lies within the range 1 g to 250 g.

10. The medical sealant member according to claim 9, wherein said polydimethylsiloxane is present in an amount of 100 to 300 parts by weight per 100 parts by weight of linear polyorganosiloxane.

11. The medical sealant member according to claim 9, wherein said polydimethylsiloxane has a viscosity in the range of 20 cs to 1,000 cs.

* * * * *